(12) United States Patent
Weber et al.

(10) Patent No.: US 9,872,982 B2
(45) Date of Patent: Jan. 23, 2018

(54) ELECTROOSMOTIC CONVECTION-ENHANCED DELIVERY SYSTEM

(71) Applicant: University of Pittsburgh—Of the Commonwealth System of Higher Education, Pittsburgh, PA (US)

(72) Inventors: Stephen Weber, Allison Park, PA (US); Amir H. Faraji, Pittsburgh, PA (US); Yifat Guy, Newtown Square, PA (US); Andrea Jaquins-Gerstl, Oakdale, PA (US); Alec C. Valenta, South Park, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 831 days.

(21) Appl. No.: 13/738,720

(22) Filed: Jan. 10, 2013

(65) Prior Publication Data

US 2013/0178788 A1 Jul. 11, 2013

Related U.S. Application Data

(60) Provisional application No. 61/584,972, filed on Jan. 10, 2012.

(51) Int. Cl.
*A61N 1/32* (2006.01)
*A61N 1/30* (2006.01)
*A61M 37/00* (2006.01)

(52) U.S. Cl.
CPC ............. *A61N 1/325* (2013.01); *A61M 37/00* (2013.01); *A61N 1/306* (2013.01); *A61M 2037/0007* (2013.01)

(58) Field of Classification Search
CPC .......... A61M 37/00; A61M 2037/0007; A61N 1/325; A61N 1/30; A61N 1/306
See application file for complete search history.

(56) References Cited

U.S. PATENT DOCUMENTS 3,630,198 A * 12/1971 Henkin ............... A61M 25/065
604/170.01
5,162,042 A * 11/1992 Gyory ................... A61N 1/044
604/20
(Continued)

FOREIGN PATENT DOCUMENTS

EP 0333356 A2 * 9/1989 ........... C07K 14/815

OTHER PUBLICATIONS

Seunguk, O. H., et al. "Improved distribution of small molecules and viral vectors in the murine brain using a hollow fiber catheter." Journal of neurosurgery 107.3 (2007): 568.*
(Continued)

*Primary Examiner* — Bhisma Mehta
*Assistant Examiner* — Nilay Shah
(74) *Attorney, Agent, or Firm* — Klarquist Sparkman, LLP

(57) ABSTRACT

Apparatuses and methods for electrokinetic transport of fluids to patients. Drug-containing solutions may be placed in vial-like reservoir, which is connected to an apparatus such as a traditional catheter or other device capable of holding a drug-containing solution. Instead of a vial-like reservoir, a doped infusion pad or a gel may be used as a source of the drug-containing solution. The reservoir and apparatus may thus be the same component. The methods and apparatuses disclosed herein may also be used to transport fluid alone to achieve a clinical effect. The apparatus is placed at the point of drug delivery. The counter-electrode may be placed in or on a patient. Current is passed from the reservoir to the counter-electrode. Through elec- (Continued)

trokinetic transport, drug-containing solution is delivered along a current path from the drug source to the counter-electrode. A hollow fiber catheter for use in electrokinetic transport is also disclosed.

18 Claims, 8 Drawing Sheets

(56) References Cited

U.S. PATENT DOCUMENTS

| | | | | |
|---|---|---|---|---|
| 5,328,471 A * | 7/1994 | Slepian | ............... | A61L 24/0031 128/898 |
| 5,458,568 A * | 10/1995 | Racchini | ............. | A61M 25/104 604/103.01 |
| 5,591,139 A * | 1/1997 | Lin | ................... | A61M 37/0015 604/264 |
| 6,322,534 B1 * | 11/2001 | Shkolnik | ............. | A61M 25/005 604/96.01 |
| 6,334,856 B1 * | 1/2002 | Allen | ................... | A61B 5/1411 128/898 |
| 6,461,331 B1 * | 10/2002 | Van Antwerp | ......... | A61K 38/28 514/35 |
| 2002/0065533 A1 * | 5/2002 | Weaver | ................ | A61M 5/427 606/191 |
| 2003/0060798 A1 * | 3/2003 | Fischer | ................... | A61N 1/30 604/501 |
| 2004/0106951 A1 * | 6/2004 | Edman | .................... | A61N 1/05 607/2 |
| 2007/0066934 A1 * | 3/2007 | Etheredge, III | .. | A61M 37/0015 604/46 |
| 2007/0154476 A1 * | 7/2007 | Browning | .......... | C07K 16/2878 424/144.1 |

OTHER PUBLICATIONS

Guy et al., "Iontophoresis from a micropipette into a porous medium depends on the ζ-potential of the medium," *Anal. Chem.* (2012).

Stoppini et al., "A simple method for organotypic cultures of nervous tissue," *J. Neurosci. Methods* 37(2):173-82 (1991).

Guy, Y. et al., "Determination of zeta-potential in rat organotypic hippocampal cultures," *Biophysical Journal* 94:4561-9 (2008).

Guy et al., "Determination of zeta-potential and tortuosity in rat organotypic hippocampal cultures from electroosmotic velocity measurements under feedback control," *Anal. Chem.* 81:3001-7 (2009).

Ungerstedt, "Microdialysis—principles and applications for studies in animals and man," *J. Intern. Med.* 230:365-373 (1991).

Oh et al., "Improved distribution of small molecules and viral vectors in the murine brain using a hollow fiber catheter," *J. Neurosurg.* 107(3):568-77 (2007).

Kim et al., "A voxelized model of direct infusion into the corpus callosum and hippocampus of the rat brain: model development and parameter analysis," *Med. Biol. Eng. Comput.* 48:203-14 (2010).

Støverud et al, "Modeling concentration distribution and deformation during convection-enhanced drug delivery into brain tissue," *Transport in Porous Media* 92:119-43 (2012).

Amir Hussein Faraji, "Convection-Enhanced Delivery of Macromolecules to the Brain Using Electronkinetic Transport," University of Pittsburgh (2011).

* cited by examiner

ELECTROOSMOTIC CONVECTION-ENHANCED DELIVERY SYSTEM

RELATED APPLICATIONS

This application claims the benefit under 35 U.S.C. § 119(e) of the earlier filing date of U.S. Provisional Application Ser. No. 61/584,972 filed on Jan. 10, 2012.

GOVERNMENT SUPPORT

This invention was made with government support under GM044842 and RR024153 awarded by the National Institutes of Health. The government has certain rights in the invention.

BACKGROUND OF THE INVENTION

1. Field of the Invention

The present invention relates generally to the field of delivery of fluids and/or drugs to tissue, particularly to the electroosmotic delivery of fluid and/or drugs or other solutes to brain tissue.

2. Description of the Background

Drugs (e.g., biologically active small molecules, antibodies, nanoparticles) are administered to humans to treat a diversity of pathophysiological or disease states. Specific formulations for intravenous, oral, or other routes of administration are employed to deliver those drugs or solutes to patients or in research settings with animals or other biological systems. However, due to a variety of factors, including a limited ability of some drugs to pass across blood vessel walls (e.g., the blood-brain-barrier), direct administration of the drug to the target tissue itself is required.

Direct administration of a biologically active agent is traditionally accomplished by injection of a bolus of the drug or solute into the tissue of interest. Such convective flow procedures are accompanied by numerous complications. For example, the injection of fluid may cause damage to the tissue through physical deformation, both at the site of injection and along the path traversed by the cannula, resulting in the death or abnormal functioning of healthy tissue. Moreover, direct injection may not be effective due to a lack of penetration of the drug into certain dense target tissues (e.g., tumors) due to hypercellularity, altered tissue architecture, etc. Additionally, bulk injections of drug-containing fluid often results in backflow of fluid into and around the injection cannula, further reducing its potential efficacy and distribution.

Brain tumors represent a particularly appropriate target for direct drug administration. Malignant gliomas account for approximately 70% of new malignant primary brain tumor diagnoses each year in the United States. Moreover, gliomas are associated with disproportionately high morbidity and mortality, with only a 12 to 15 month median survival for patients with glioblastomas and 2 to 5 years for patients with anaplastic gliomas, irrespective of treatment. Gliomas represent a category of malignant primary brain tumors that originate from the supporting cells—oligodendrocytes and astrocytes—of the central nervous system. Recurrence of gliomas at the same or adjacent anatomical sites is routine observed. Such a pathological condition would indicate a benefit to a sustained and direct administration of chemotherapeutic agents.

Brain tissue also presents particular problems for convective, bolus injections of drug-containing fluids. Pressure-driven convection-enhanced delivery of solutions in clinical trials elucidated several complications related to controlling the direction of fluid flow. In these trials, infusions followed paths of least pressure resistance (which did not usually coincide with their target path), and often penetrated ependymal linings with uncontrolled ejections into the ventricular system, flowed backwards along the infusion cannula, or deformed brain tissue itself.

In contrast, electrokinetic transport of compounds provides a more controlled and reproducible mechanism for delivery of drugs to biological tissue. Electrokinetic transport in human or animal tissue represents the movement of molecules due to an applied electric field including electroosmosis and electrophoresis. Electroosmosis is the bulk fluid flow developed in a porous matrix with a non-zero zeta-potential, such as brain or other human or animal tissue, upon application of an electric field, while electrophoresis is the movement of a charged molecule itself in the electric field. Electrokinetic transport avoids many of the complications encountered in the traditional bulk injection of drugs into tissue in that it does not involve the pressure injection of large volumes of fluid into tissue. Furthermore, unlike pressure-induced convection-enhanced delivery, neither the porosity of the tissue being penetrated or the characteristic dimensions of the extracellular space are dominant factors in penetration depth of the drug. Transport is instead predominantly guided by the chemical properties of the drug and tissue rather than by the physical structure of the porous medium.

The present invention addresses the deficiencies of the prior art by providing a novel mechanism by which drugs may be administered to a patient in need thereof. The present invention takes advantage of the chemical properties of drugs, solutes, and target tissue to provide a mechanism for delivering a carefully controlled amount of drug to a target tissue, while minimizing problems associated with traditional bolus administration. The delivery methods and apparatuses of the present invention may be employed in a wide variety of physiological, research, and medical situations.

SUMMARY OF THE INVENTION

The present invention encompasses methods of administering solutions to a patient in need via electrokinetic transport. The present invention takes advantage of the electrochemical properties of solutions to deliver fluids through application of electrical current. The solution may contain a charged or uncharged biologically active compound, such as a small molecule, antibody, peptides, steroids, or other compounds, to a patient. In other embodiments, the present invention may be used to transport fluid to a patient to achieve a clinical effect.

When delivering a solution containing a drug, the present invention may use any drug-containing reservoir, such as a bottle or vial. The reservoir may also be a material that absorbs or entrains the solution of a drug, such as an infusion pad or a gel. The drug-containing reservoir acts as a source for the drug to be delivered to the patient. The drug-containing reservoir should contain a path that allows drug-containing fluid to escape the reservoir into the tissue. When the reservoir is a vial or bottle or similar container, an implantable apparatus is employed to deliver the drug to the patient. The apparatus may take the form of any device having an opening/passage that allows movement of drug-containing fluid from the device into the patient, such as a traditional open-tube catheter or hollow fiber catheter. When the reservoir is a pad or gel, the drug-containing fluid emanates from the pad or gel directly into the tissue. In this case the reservoir and apparatus may be the same component. Electrokinetic transport of drug is achieved by placing a counter-electrode in the subject at some distance from the point at which drug-containing fluid is delivered to the patient. Both the counter-electrode and drug-containing reservoir are connected to a current source. By passing current from the drug-containing reservoir to the counter electrode, drug-containing fluid is electrokinetically transported from the reservoir to the tissue. The shape of the trajectory of the drug delivery may be set by the relative placement of the infused pad, gel, or catheter and the counter-electrode. The current path to the counter-electrode may be through a second catheter called a counter-catheter. The current path to the counter-electrode may be through a gel or pad in contact with the patient. The various catheters, pad, or gels can be implanted for either short or long periods of time.

The present invention also encompasses apparatuses for use in the electrokinetic delivery of drug-containing fluids to patients in need thereof. One embodiment of the apparatuses of the present invention includes an open tube catheter, where the drug-containing reservoir includes a tube that allows fluid to flow from the vial portion of the reservoir to the distal end of the catheter portion of the reservoir that is placed into the patient at the point of drug delivery. The distal end of the catheter portion of the reservoir includes a path that allows drug-containing fluid to escape the catheter. The proximal end of the catheter may include a larger reservoir containing the fluid to be delivered and an electrode compartment for connection to the counter-electrode circuitry. The electrode compartment and the drug-containing reservoir are preferably separated from one another so as to avoid any electrochemical reaction of the drug in the reservoir. The counter-electrode may be connected to the patient through a catheter, as a conductive pad on the skin of the patient, or as a bare wire among other implementations. Both the catheter and the counter-electrode may be connected to a current generator. By passing current from the catheter to the counter-electrode/catheter drug-containing fluid may be delivered to the patient by electrokinetic transport.

Another embodiment of the apparatuses of the present invention includes a hollow fiber catheter, where the drug-containing reservoir comprises a tube that allows fluid to flow from the vial portion of the reservoir to the distal end of the catheter portion of the reservoir that is placed into the patient at the point of drug delivery. The distal end of the catheter portion of the reservoir is a hollow fiber which includes multiple parallel paths that allow drug-containing fluid to escape the catheter. The proximal end of the catheter may include a larger vial-type reservoir containing the fluid to be delivered and an electrode compartment for connection to the counter-electrode circuitry. The electrode compartment and the drug-containing reservoir are preferably separated from one another so as to avoid any electrochemical reaction of the drug in the reservoir. The counter-electrode may be connected to the patient through a catheter, as a conductive pad on the skin of the patient, or as a bare wire among other implementations. Both the catheter and the counter-electrode may be connected to a current generator. By passing current from the catheter to the counter-electrode/catheter drug-containing fluid may be delivered to the patient by electrokinetic transport.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF THE INVENTION

Figure 1:
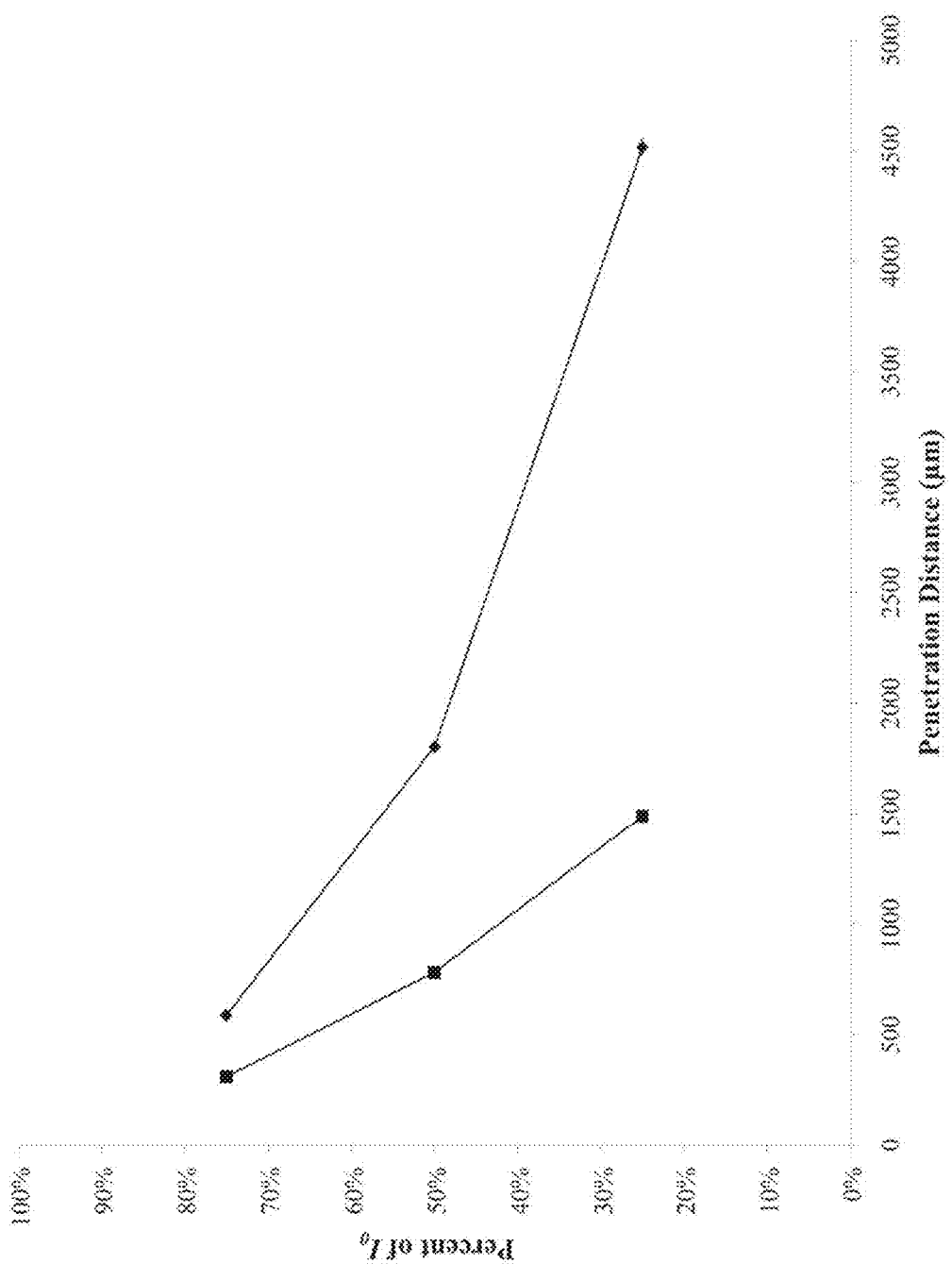
FIG. 1 shows the effect of the size of the opening of the fused silica open tube catheter on penetration distance into a hydrogel.

It is to be understood that the figures and descriptions of the present invention have been simplified to illustrate elements that are relevant for a clear understanding of the invention, while eliminating for purposes of clarity, other elements that may be well known. The detailed description will be provided hereinbelow with reference to the attached drawing.

The present invention provides a framework, methods, and apparatuses for applying electrokinetic transport to the effective delivery of fluids and/or drugs or other solutes to target tissue, while at the same time limiting complications that arise from traditional bolus injections and pressure-driven convection-enhanced delivery. While the following description of the invention provides specific examples within the context of brain tumors, that should not be construed as limiting the invention. The present invention is equally useful in the administration of drugs or other solutes to or the transport of fluid within any target tissue in human or animal subjections that are in need thereof.

The term "drug" is employed in the context of the present invention to encompass any protein, nucleotide, small molecule, lipid, or other chemical that may have an effect on biological tissue. As such, "drug" may mean such agents as chemotherapeutic compounds, local anesthetics, antibodies, signaling peptides, steroids, and neurotransmitters. Small delivery vehicles such as nanoparticles and liposomes are also contemplated as being useful within the context of the present invention. One of skill in the art will recognize that many compounds will be appropriate for the given implementation of the present invention. Additionally, the present invention may be used to simply transport fluid through or from a selected tissue, which may be useful in relieving tissue edema or swelling. Additionally, the present invention may be used to transport fluid from one region of tissue to an adjacent region of tissue.

The present description employs the term "catheter" to encompass a generic class of fluid delivery components. The catheter may be any tube, capillary, or cannula, and it may contain a matrix, porous material, fluid-containing reservoir, or combinations thereof that allow transport of fluid or drug into the targeted tissue via the methods and apparatuses disclosed herein. The present invention may preferably employ any material that contains fluid conduits and has a negative or zero zeta potential.

The present invention provides numerous benefits over the prior art. Specifically, the present invention avoids backflow of drug-containing solution along a drug delivery tube or cannula that is commonly observed in traditional convection-enhanced delivery. Additionally, minimal tissue deformation and subsequent cell death is caused by the use of the present invention. The present invention also allows for reproducible delivery of a drug in which the directionality of the delivery is well controlled. Penetration of tissues resistant to pressure-induced fluid flow, i.e., those with low hydraulic permeability, may also be achieved by employing the present invention. Furthermore, controlled perfusion of areas of tissue near surfaces may be achieved using infusion pads of the present invention.

While not wishing to be bound to theory, electrokinetic transport is achieved by transferring drug from a catheter or other source into tissue on the basis of the electroosmotic flow in the tissue. The catheter itself may contribute to the overall flow. Electroosmotic flow results because a substance (e.g., polymer or gel), or a catheter's walls, may possess a negative charge. Examples of such polymers include acrylate- and methacrylate-containing polymers and sulfonate-containing polymers. A measureable property related to the magnitude of the gel or surface negative charge density is the zeta potential. A more negative zeta potential corresponds to a higher negative surface charge density. The counterions required for electroneutrality are positively charged and freely soluble in the liquid entrained in the gel or in the liquid in the lumen of the catheter. Examples of such catheters are glass, fused silica, polymers, metals with insulating coatings, and those with surfaces intentionally modified to be anionic, among others (unless intentionally modified to be positive, most surfaces are naturally negatively charged when in contact with water even if their chemical composition does not suggest this. For example, Teflon® has a significant negative zeta potential). By passing current through the substance or catheter to an electrode located outside of the catheter, electrokinetic transport of the counterions, and thus the solution initially entrained in the gel, or initially residing in the lumen of the catheter, into the tissue is achieved. Because of the low hydraulic permeability of brain tissue, especially in relation to a catheter, the zeta potential in the brain is the primary determinant of the overall observed flow. (Guy Y, et al., Iontophoresis From a Micropipette into a Porous Medium Depends on the ζ-Potential of the Medium. *Analytical Chemistry.* 2012, incorporated by reference) The transport of drug by the inventive method is notable in that it may be employed using a device having a small source of drug and be delivered using high currents and for long periods of time, in contrast to traditional approaches.

Experiments in Hydrogels as a Surrogate for Tissue

To investigate the scientific principles supporting the present invention, initial experiments were conducted using poly(acrylamide-co-acrylic acid) gels. Hydrogels were synthesized to mimic the electrokinetic properties of organotypic hippocampal slice cultures (OHSC), as a surrogate for brain tissue. The zeta-potential of a 25% (100×weight of acrylic acid/(weight of acrylamide plus "bis" (N,N'-methylenendiacrylamide) plus acrylic acid) hydrogel mimicked the zeta-potential of neural tissue and was used in many experiments.

Fused silica open tube catheter infusions of molecules into the hydrogels and OHSC provided a framework to understand the relevant experimental parameters, such as the effect of varying the catheter tip size, applied electrical current, zeta-potential of the catheter or the tissue surrogate, infusion time, tortuosity of the tissue surrogate, and properties of the solute (including molecular weight and electrophoretic mobility).

To deliver solutes into the surrogate tissue, fused silica catheters of two types were used: (1) 50.0±0.1 μm inner diameter, 358.5±1.5 μm outer diameter, length 10 cm and (2) 99.5±0.2 μm inner diameter, 361.1±0.7 μm outer diameter, length 10 cm and were cleanly cut to a blunt tip with the same dimensions. The catheter was filled with an electrolyte solution containing 45 mM of the solute $Ru(bpy)_3^{2+}$ (bpy=2, 2'-bipyridine; a small fluorescent molecule, MW—570, chloride salt).

The fused silica catheter was carefully positioned into the surrogate tissue. The distal end of the catheter is inserted into the tissue. The proximal end of the fused silica catheter was immersed in a vial containing buffer solution and a silver working electrode. Additionally, a silver wire ground electrode (0.3 mm diameter) was inserted into the surrogate tissue, so that the distance between the catheter tip and the ground electrode was always more than 5 mm. Placing the ground electrode this distance from the catheters with tip openings of the sizes used insures that distribution of solute outside the tip will be approximately symmetrical. A current source was used to create electroosmotic flow from the catheter into the surrogate tissue. The direction of fluid flow is controlled by the sign of the zeta-potential and the sign of the current. For the catheters, hydrogels (tissue surrogates and infusion pads), and tissues used here, the zeta-potential is negative. Fluid flow will thus travel in the same direction as a positive current. A positive current moves in the same direction as positively charged particles. Distribution of the solute was imaged using standard digital microscopy techniques.

$Ru(bpy)_3^{2+}$ was infused from each catheter for up to 40 minutes, with results shown in FIG. 1. FIG. 1 displays the effect of catheter tip size on penetration distance (μm) of $Ru(bpy)_3^{2+}$ from 1 μA infusions for 40 min in a hydrogel with −24.7 mV zeta-potential: square, 50 μm diameter tip (N=5), diamond, 100 μm diameter tip (N=5). Intensities are normalized to the intensity outside the tip of the catheter in the surrogate tissue, $I_0$. The penetration distance where the fluorescence intensity was 25% of $I_0$ occurred at 4,516±96 μm (number of experiments, N=5) away from the 100 μm diameter catheter tip opening and at 1,489±27 μm (N=5) away from the 50 μm diameter catheter tip opening (data are presented as means±SEM). There was only an approximately 2% variation in the penetration distances, indicating the highly reproducible nature of the infusion profile. In the literature on pressure-motivated convection-enhanced delivery, the volume of substance delivered is determined from the distance away from the source at which the concentration of the solute being delivered is 10% of that at the tip. Within the context of the present experiments, the distance away from the source at which the intensity (concentration) is 25% of that at the tip is measured because it can be assessed more accurately than the distance at 10%. The distance to the 10% point is certainly greater than the distance to the 25% point.

Figure 2:
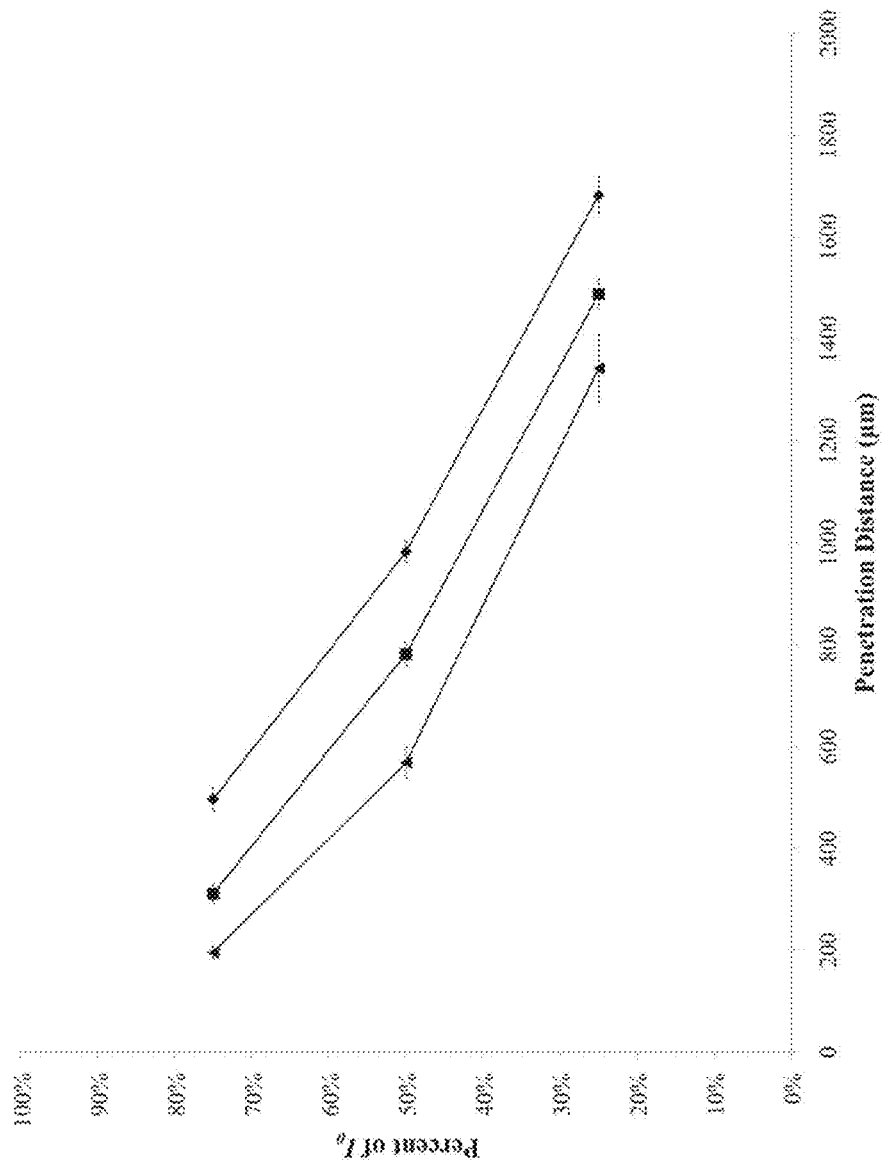
FIG. 2 displays the effect of applied current on penetration depth.

With a particular catheter tip size (~50 μm diameter) and the same $Ru(bpy)_3^{2+}$ infusate, experimental time, and hydrogel conditions, only the applied electrical current was varied. As shown in FIG. 2, the penetration distance increased predictably over a range of currents from 0.5 to 1.5 μA, for percentages of $I_0$ equal to 75%, 50%, and 25%. Over this narrow range of applied currents, the distances where 25% of $I_0$ occurred are 1,342±67 µm (N=5) away from the catheter tip and 1,682±36 µm (N=5) away from the catheter tip after 40 minutes of infusion for 0.5 and 1.5 µA currents respectively. In FIG. 2, the following indications are used: triangle, 0.5 µA (N=5), square, 1.0 µA (N=5), diamond, 1.5 µA (N=5). As shown, there was only an approximately 2 to 5% variation in the penetration distances, indicating the highly reproducible nature of the infusions. The ratio of the penetration distance at 25% of $I_0$ of the electrokinetic transport of $Ru(bpy)_3^{2+}$ to the maximum distance that the molecules could travel by diffusion alone (i.e., at the steady state) was 14 and 17 for the 0.5 and 1.5 µA currents respectively. Thus, increasing the applied electrical current resulted in greater perfusion distances in hydrogels.

Experiments in OHSC

Figure 3:
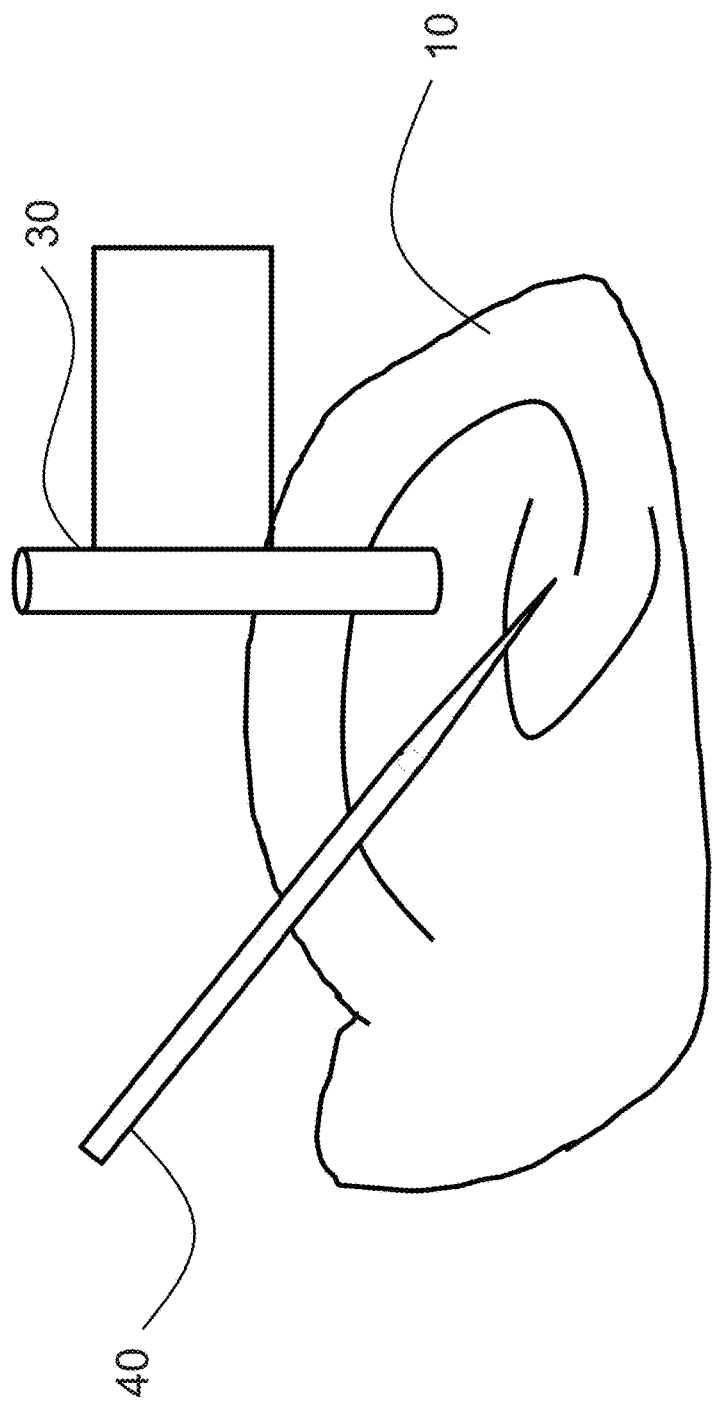
FIG. 3 depicts the configuration of electrodes used in some experiments in organotypic hippocampal slice cultures.

Additional delivery experiments were conducted in slice cultures, shown in FIG. 3. Organotypic hippocampal slice cultures (OHSC; 10) were generated according to the procedure of developed by Stoppini et al. (Stoppini, L.; Buchs, P. A.; Muller, D., "A simple method for organotypic cultures of nervous tissue." *J. Neurosci. Methods* (1991) 37 (2):173-82, which is hereby incorporated by reference). Infusion catheters were prepared from fused silica catheters by pulling them to a tip (opening approximately 20 µm in diameter) using a laser capillary puller. The infusion catheter 40 was filled with the fluorescent solute solution. The infusion catheter was guided into the CA3 region of the OHSC by a micromanipulator arm. The counter catheters (99.5±0.2 µm inner diameter, 361.1±0.7 µm outer diameter, length 10 cm) were cleanly cut to a blunt tip with the same diameter dimensions. A counter catheter 30 was positioned at a 90° angle relative to the plane of the OHSC using another manipulator arm. The tip was placed onto the CA1 region of the OHSC. The proximal end of each catheter was immersed in a vial containing buffered physiological electrolyte solution and a silver working electrode (not shown). A current source was used to drive the delivery of solute from catheter 40 into tissue 10 and the penetration of the compound into the gel was imaged using standard fluorescence microscopy techniques.

Figure 4:
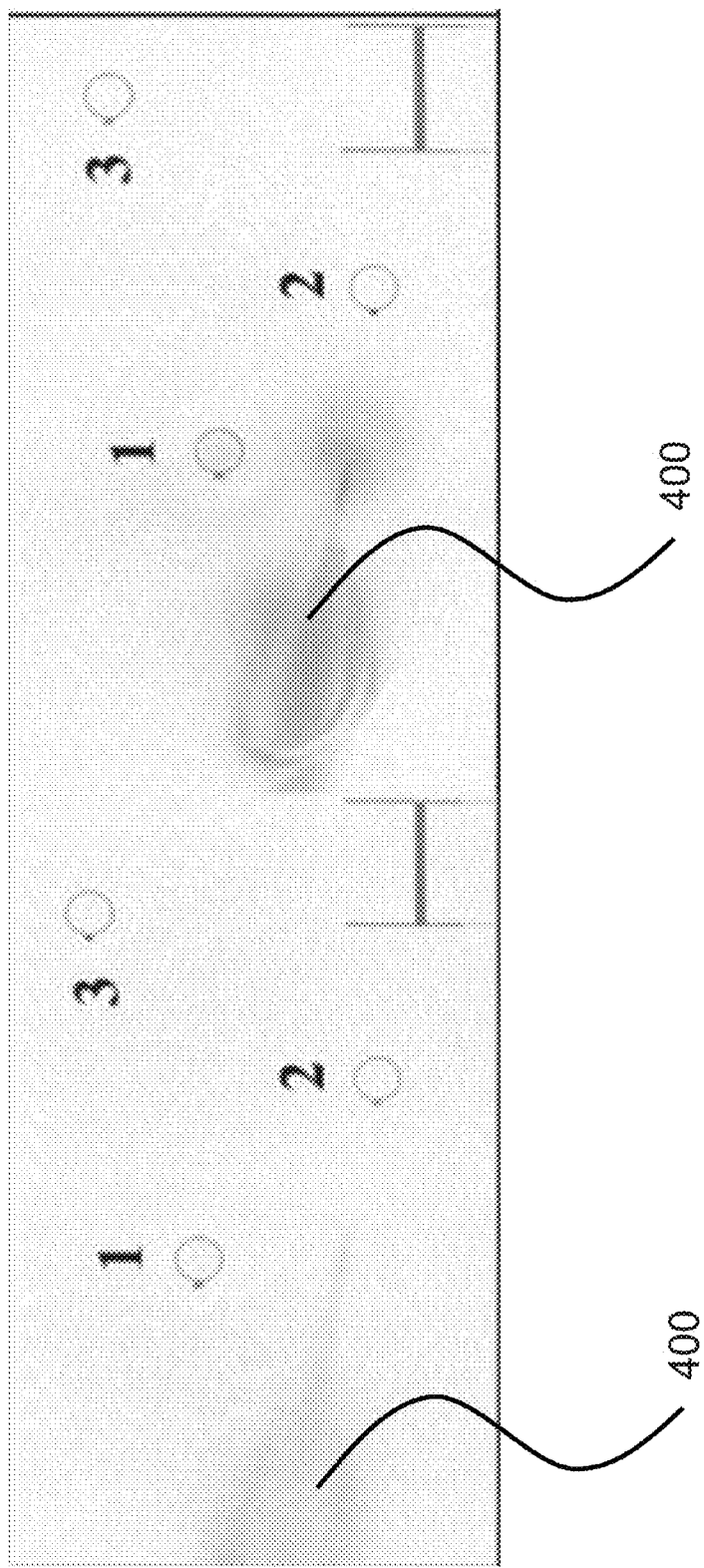
FIG. 4 shows an image collected during an experiment in organotypic hippocampal slice cultures.

The ability to control the directional path of catheter infusions with counter-electrode/catheter placement was examined. FIG. 4 shows images of experiments using more than one catheter in OHSC with 0.3 µA of applied current. The pulled (20 µm diameter opening) infusion catheter 400 is visible on the left side of each panel. It is filled with a Texas Red-dextran conjugate of 70 kDa molecular weight (TR70). It has been inserted at the dorsal tip of the dentate gyrus at a 20° angle to the OHSC surface. A 100 µm inside diameter counter-catheter is filled with buffered physiological electrolytes and inserted approximately 420 µm away at the interface between CA1 and CA3 at a 90° angle to the OHSC surface, labeled 1. Intensity was measured at circles 1, 2, and 3. The left panel (FIG. 4A) was at the beginning of the experiment and the right panel (FIG. 4B) is following 20 minutes of applied current. The fluorescence intensities were determined in each region of interest (labeled with numbers), denoted by the circles. The scale bar is 350 µm. FIG. 4 shows that the fluorescence intensity is greater at region 1 than at equidistant region 2. The fluorescence intensity at region 2 is similar to that at region 3. This demonstrates the bending of a solute's path over more than 400 µm, as the TR70 solution in buffer solution was infused from the smaller catheter tip to the 100 µm diameter counter-electrode in an OHSC, as depicted in FIG. 3. In this example, TR70 was transported along a current path towards the counter-electrode, with no backflow along the infusion catheter. Moreover, because TR70 has a very low electrophoretic mobility, this anisotropic transport was predominantly due to electroosmosis. A roughly spherical infusion profile was seen if the counter-electrode was placed remotely. The ejection profile obtained in this experiment is unusual because of the dramatic bending towards the counter-electrode, which cannot be a result of diffusion.

A defined current path affords greater control of electrokinetic infusion and addresses a key limitation of pressure-induced convection enhanced delivery borne out through clinical trials. The counter-catheter should not be positioned at any distance away from the infusion catheter, however. The electric field away from a point source is proportional to $1/r^2$ (where r is the distance away), and therefore decays rapidly from the catheter tip. It is reasonable to conclude that electrokinetic transport might not occur when the electric field becomes zero, and as the electric field diminishes at further distances, the rate of electrokinetic transport decreases.

In a second experiment, the counter-catheter was replaced with a silver wire (0.3 mm diameter) as the counter-electrode and inserted into CA3 of an OHSC. The 20 µm pulled infusion catheter was replaced with a 100 µm unpulled infusion catheter filled with a 45 mM $Ru(bpy)_3^{2+}$ solution in buffer solution. The infusion catheter was placed onto CA1 perpendicular to the plane of the OHSC. As the diameter of the infusion catheter tip was significantly increased in this example, the corresponding electric field emanating from the tip was expected to remain appreciable at much further distances in the OHSC. The infusion of $Ru(bpy)_3^{2+}$ displays a bent path towards the counter-electrode and increased fluorescence within the OHSC after 25 minutes of 1.5 µA current applied.

As a control to demonstrate the effect of counter-electrode/catheter placement, the counter-electrode was placed remotely by immersing it in the buffer solution beneath the insert membrane that supports the OHSC. Under these conditions, the preferential transport of $Ru(bpy)_3^{2+}$ through the OHSC was abolished, and the fluorescence was instead localized around the catheter tip in an approximately isotropic manner, with a diminished fluorescence intensity within the OHSC.

Figure 5:
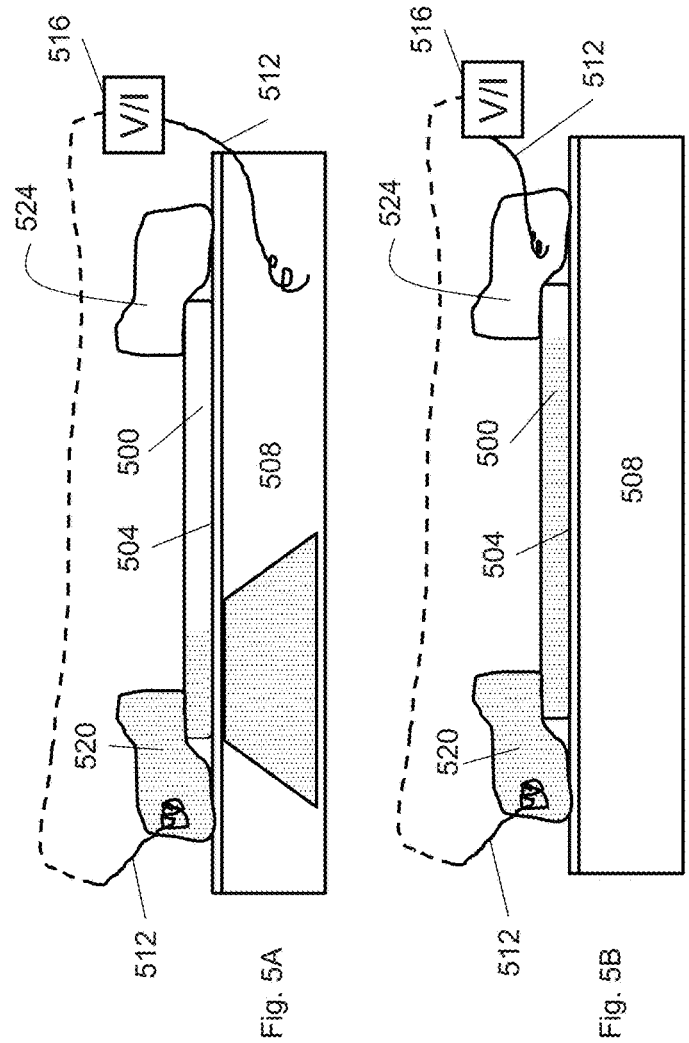
FIG. 5 displays a configuration for experiments performed using hydrogels in organotypic slice cultures.

Because of issues with backflow and lack of directional control associated with pressure-driven convection-enhanced delivery, only deep areas of the brain may be targeted by those prior art techniques. For example, one can intuitively imagine that surface ejections using pressure would cause the infusate to spread across the cortical surface without deep penetration of the underlying tissue. To address this limitation by using electrokinetic delivery, a hydrogel with a zeta-potential similar to brain tissue (e.g., OHSC) was used as an infusion pad to deliver a solute over wide areas. Further experiments were performed in which an infusion pad containing a fluorescent solute was used to introduce the marker into an OHSC. A 25% acrylic acid poly(acrylamide-co-acrylic acid) infusion pad was placed in a solution of 0.5 mM Texas Red labeled 3 kDa dextran (TR3) in buffer, and allowed to equilibrate overnight. The doped infusion pad was removed from the solution and cut to a size of 3 mm×3 mm at the base×2 mm high. The infusion pad was placed over the subiculum and entorhinal cortex portions of an OHSC on its culture insert membrane. A second 25% acrylic acid poly(acrylamide-co-acrylic acid) infusion pad that did not contain fluorescent solute (only buffer solution) was placed over the opposite border of the OHSC, just adjacent to the CA3 region. The distance between the doped and undoped infusion pads was 1.5 mm. A 0.3 mm diameter silver wire was placed into each infusion pads. A current source was used to drive the delivery of compound from the infusion pad containing the fluorescent solute towards the undoped one, and the penetration of the compound into the gel was imaged using standard fluorescence microscopy techniques. The configuration of the experiment is shown in FIG. 5. Tissue culture 500 sits on membrane 504 above medium or physiological buffer 508. Electrodes 512 attached to a power source with controllable voltage or current 516 cause current to flow from solute-loaded gel 520 either (FIG. 5A) into the medium/buffer 508 because the counter-electrode resides there, or (FIG. 5B) into the tissue 500 when the counter-electrode resides in the other piece of gel 524.

Figure 6:
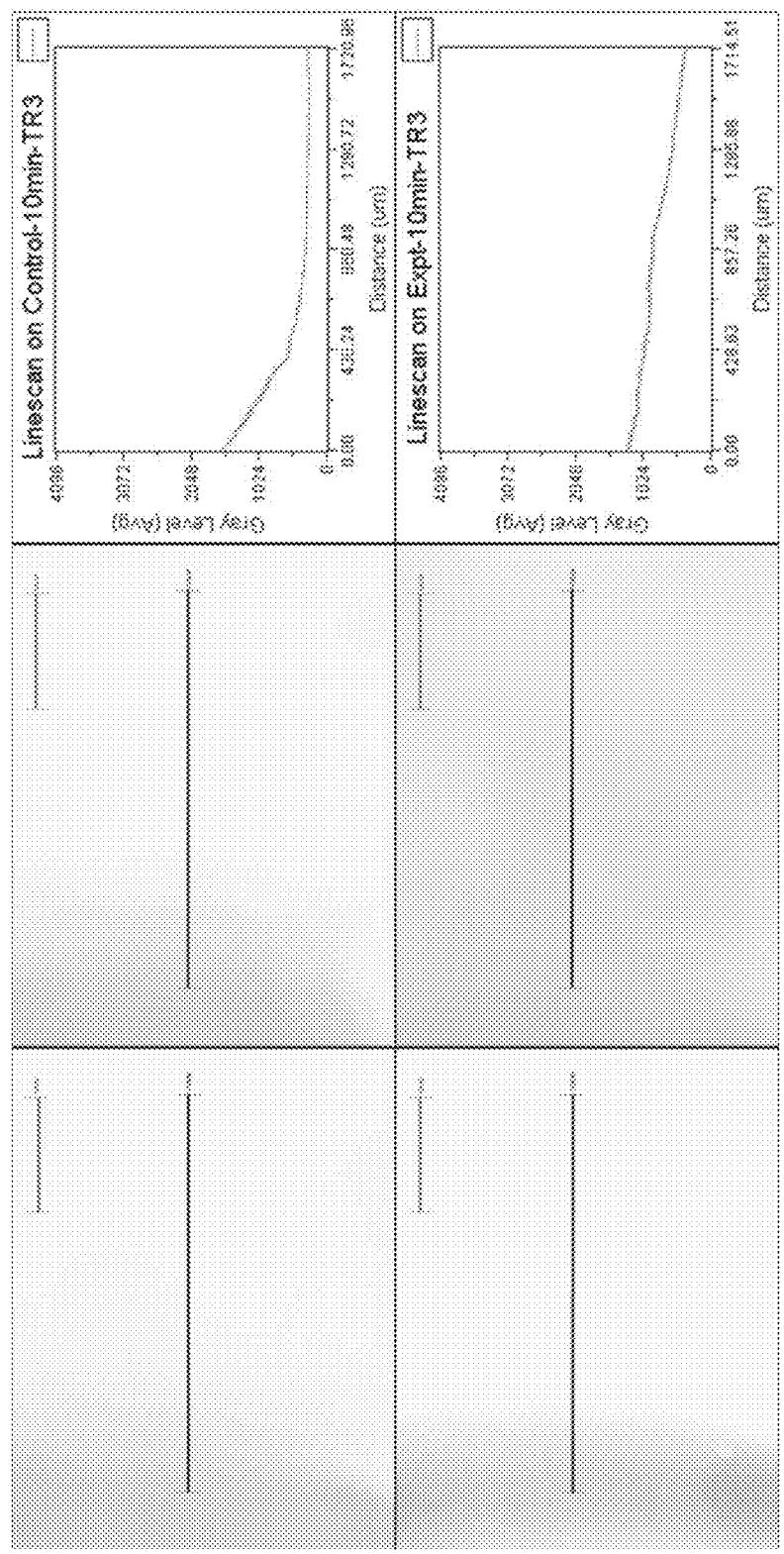
FIG. 6 shows an image collected during an experiment in organotypic slice cultures using a hydrogel.

FIG. 6 shows fluorescence images of results. The left two panels show the fluorescent infusion pad on the left before the current is applied. With an applied current of 10.0 μA (positive current going left to right), TR3 was transported across the entire OHSC (distance ~1,500 μm) over a period of 10 minutes. This can be seen in the lower right panel.

The horizontal linescans provided quantification of the TR3 fluorescence intensity passing through the OHSC. When the current path passed through the OHSC, the linescan revealed the penetration distance at 25% of $I_0$ to be approximately 1,260 μm away from the doped infusion pad, almost fully across the distance between the two infusion pads. In contrast, when the current was directed away from the OHSC, and instead through the insert membrane to the buffer solution below (FIG. 6, upper right panel), the penetration distance at 25% of $I_0$ occurred at nearly 320 μm away from the doped infusion pad. Similar to the results presented above for catheters and OHSC, the electrical current path may be used to control the path of electrokinetic transport using infusion pads.

This experiment also provided evidence that larger tissue areas may be impacted by doped infusion pad delivery, in a faster time and at higher currents, than by catheter infusions. This is partly due to a striking difference in the decay of the electric field within the OHSC. In the geometry shown in FIG. 6, the solute is not delivered from a small (with respect to the distance that the solute travels during its delivery) hemispherical source. Instead, the electric field between the two infusion pads can be better approximated by the electric field between two conducting plates. Neglecting edge effects, the electric field between the plates is constant. Furthermore, the distance between the conducting plates is one parameter that determines the magnitude of the electric field. As the dimensions of the bases of the doped and counter infusion pads were larger than the OHSC edge effects can be ignored. Thus, the electric field was roughly constant throughout the OHSC between the infusion pads.

Experiments In Vivo

Additional experiments were conducted in vivo in rats to demonstrate the electroosmotic delivery of a fluorescent solute into the intact thalamus. Male Sprague-Dawley rats, with weights ranging from 260 to 290 g, were anesthetized with isoflurane, and wrapped in a 37° C. homeothermic blanket. An incisor bar was set at 0 mm at the interaural line. Rats underwent aseptic stereotactic surgery, whereby bilateral craniotomies were made to position an infusion catheter and counter catheter into the thalami bilaterally (from bregma: 4.0 mm lateral, 1.3 mm posterior, and 5.0 mm below the dura) for volumetric analysis. The capillaries were also implanted into the hippocampi bilaterally (from bregma: 4.0 mm lateral, 1.3 mm posterior, and 2.5 mm below the dura).

Fused silica catheters (99.5±0.2 μm inner diameter, 361.1±0.7 μm outer diameter, length 15 cm) were cleanly cut to a blunt tip with the same diameter and were used as the two implanted catheters. The infusion catheter was filled with the solute solution of interest: a 45 mM solution of $Ru(bpy)_3^{2+}$ in buffer solution or a co-solution of 0.1 mM TR70 and 0.1 mM BODIPY 10 in buffer solution. The counter-catheter was filled with buffer solution. The proximal ends of the fused silica catheters were immersed into a vial containing the same solute solution or buffer solution for the infusion and counter-catheters respectively. Silver wire electrodes were inserted into each of these vials and a current source was used to drive the delivery of compound from the drug catheter. Experiments used 25.0 μA of applied current for 45 minutes.

After the electrokinetic infusion period, the rats underwent rapid transcardial perfusion with 250 mL of 8% cold paraformaldehyde in PBS. The brain was immediately isolated, sectioned into 4 mm coronal slices, and then further sectioned on a vibratome into 300 μm thick coronal slices. Vibratome sectioning was quantitative, with no discarded tissue between slices with a visible fluorophore spot. The time required for the transcardial perfusion and vibratome sectioning was less than 30 minutes, while the transcardial perfusion itself was completed in less than 5 minutes. The 300 μm thick coronal slices were mounted onto glass slides and imaged with an inverted fluorescence microscope. Image sequences were acquired and the fluorescent intensity was measured.

The volumes of distribution from the infusions were determined by evaluating the fluorescence intensities amongst the coronal tissue slices. The overall maximum fluorescence intensity ($I_0$) at the infusion catheter implantation site was determined for each rat. The counter catheter placement (contralateral hemisphere) is far enough away from the delivery catheter that a symmetrical, approximately spherical distribution of solute was expected and seen in practice. The distance along eight radii was measured from a central point of maximum fluorescence intensity (in that slice) to the point where the fluorescence intensity was 25% of $I_0$. The eight radii were averaged together to arrive at a radius to determine the area of tissue impacted by the infusions, assuming a circular area. The coronal area within each slice was multiplied by the thickness of the slice to arrive at a volume per tissue slice. The volumes of each slice were summed to arrive at a final volume of distribution for each rat and fluorophore.

As noted above, three solutes of varying molecular weight and electrophoretic mobilities were utilized for in vivo infusions. BODIPY labeled 10 kDa dextran (B10) and TR70 were selected because of their dissimilar molecular weights, their ability to be resolved spectroscopically, and their small electrophoretic mobilities, as shown in Table 1 below ($V_d$ at 10% of 1 calculated as in paragraph 25). The electrophoretic mobility is the ratio of the velocity that a molecule adopts in the presence of an electric field of a particular magnitude. For comparison, the electroosmotic mobility is the velocity that the fluid adopts in the presence of an electric field. The electrophoretic mobility is directly proportional to the magnitude of the zeta potential governing the electroosmotic flow which we estimate to be −22.8 mV (Guy, Y. et al., "Determination of zeta-potential in rat organotypic hippocampal cultures." *Biophysical Journal*, (2008) 94:4561-9; Guy et al., "Determination of Zeta-Potential and Tortuosity in Rat Organotypic Hippocampal Cultures from Electroosmotic Velocity Measurements under Feedback Control." *Anal. Chem.* (2009) 81:3001-7, both of which are hereby incorporated by reference). The electroosmotic mobility of the extracellular fluid in brain is $1.7 \times 10^{-8}$ m$^2$/Vs. This is much larger than the electrophoretic mobilities of the two fluorescent dextrans in Table 1. Therefore, the volumes infused reflect electroosmosis, not electrophoresis and the difference between the volumes of tissue impacted by these two fluorescent dextran conjugates was predominantly due to the molecular weight difference. The small, cationic molecule—Ru(bpy)$_3^{2+}$—was expected to travel a much further distance than B10 or TR70 during a particular infusion time because of its relatively small molecular weight and dicationic nature (positive and large electrophoretic mobility).

TABLE 1

| Infusate | Molecular Weight | Electrophoretic Mobility ($\mu_{ep}$) ($10^{-9}$ m$^2$/Vs) | $V_d$ at 25% of $I_0$ (µL) |
|---|---|---|---|
| TR70 | 70,000 | 0.46 ± 0.03 (N = 3) | 0.60 ± 0.04 (N = 3) |
| BODIPY10 | 10,000 | −0.89 ± 0.22[21] (N = 3) | 1.71 ± 0.12 (N = 3) |
| Ru(bpy)$_3^{2+}$ | 570 | 25.86 ± 0.02 (N = 3) | 13.0 ± 2.0 (N = 4) |

In vivo ejections of the compounds in Table 1 into the rat thalamus were assessed with fluorescence microscopy. Fluorescence images were overlaid upon bright field images in order to confirm where the infusion occurred.

As shown in Table 1, the volumes of distribution ($V_d$) for the three molecules at 25% (10%) of $I_0$ were obtained with good reproducibility (data presented as means±SEM). The largest molecule evaluated, TR70, had a molecular weight of 70,000 and a very small electrophoretic mobility. The $V_d$ of TR70 fluorescence was determined as 0.60±0.04 µL, (12 µL) (N=3). B10 had a molecular weight of 10,000 and also has a very small electrophoretic mobility. The $V_d$ of B10 fluorescence was determined as 1.71±0.12 µL (35 µL) (N=3). Finally, Ru(bpy)$_3^{2+}$ was the smallest molecule evaluated, with a molecular weight of roughly 570, though its electrophoretic mobility was significant and positive as a result of its dicationic nature. The $V_d$ of Ru(bpy)$_3^{2+}$ fluorescence was determined as 13.0±2.0 µL, (260 µL) (N=4).

The variation in $V_d$ presented in Table 1 ranged from roughly 5 to 15%. Moreover, the shape of the ejection spot was only sometimes circular, and therefore approximating the area within a slice as $\pi \cdot r^2$ may not be accurate in all instances. To arrive at the value of r, eight different radii were measured at 45° intervals and averaged together. The center of each spot, from which the radii are drawn, was determined by locating the maximal fluorescence intensity. Finally, the location of the catheter implantation site was slightly variable between rats. Though injections occurred in the thalamus in all instances, there was some variability in the depth, due to differences in rat weight. If the catheter was implanted near the tissue edge of the thalamus, the radius along a particular measurement direction may theoretically be truncated with a consequently smaller area. The percent error of the volume distribution was highest for Ru(bpy)$_3^{2+}$, which most readily encountered the tissue margins due to its large ejection areas. Thus, this final point is thought to play a role in the measurement variation.

The volume of solution injected ($V_i$) was estimated based on the electroosmotic mobility in brain $\mu_{eo}$, the electrophoretic velocity of the solute, $\mu_{ep}$, the applied current, i, the conductivity of the extracellular fluid, $\sigma_{ecf}$, and a factor to account for molecular size, f, as follows:

$$U_{obs} = i \frac{(\mu_{eo} + \mu_{ep})f}{\sigma_{ecf}}$$

The flow rate with a current of 25.0 µA was therefore 0.018 µL/min. Thus, over 45 minutes, approximately 0.81 µL of the fluorophore solution was introduced into the thalamus. The fraction of the brain that is extracellular fluid varies, but is near 20%. Thus, the volume of brain tissue corresponding to 0.81 µL of fluid is 4.0 µL.

It is further noted that the currents employed in these experiments represent a fraction of those employed in deep brain stimulation experiments in humans in vivo. Thus, there is considerable opportunity to increase the amount of current that may safely be applied in electrokinetic administration of drugs into the intact brain.

In sum, the experiments described above provide a demonstration of the ability to deliver small and large molecules to slices of brain tissue, as well as to intact in vivo brains. The present invention provides such a mechanism for reproducibly and safely administering drugs to animals and humans via electoosmotic transport that does not result in deformation of the tissue and subsequent cell death.

Figure 7:
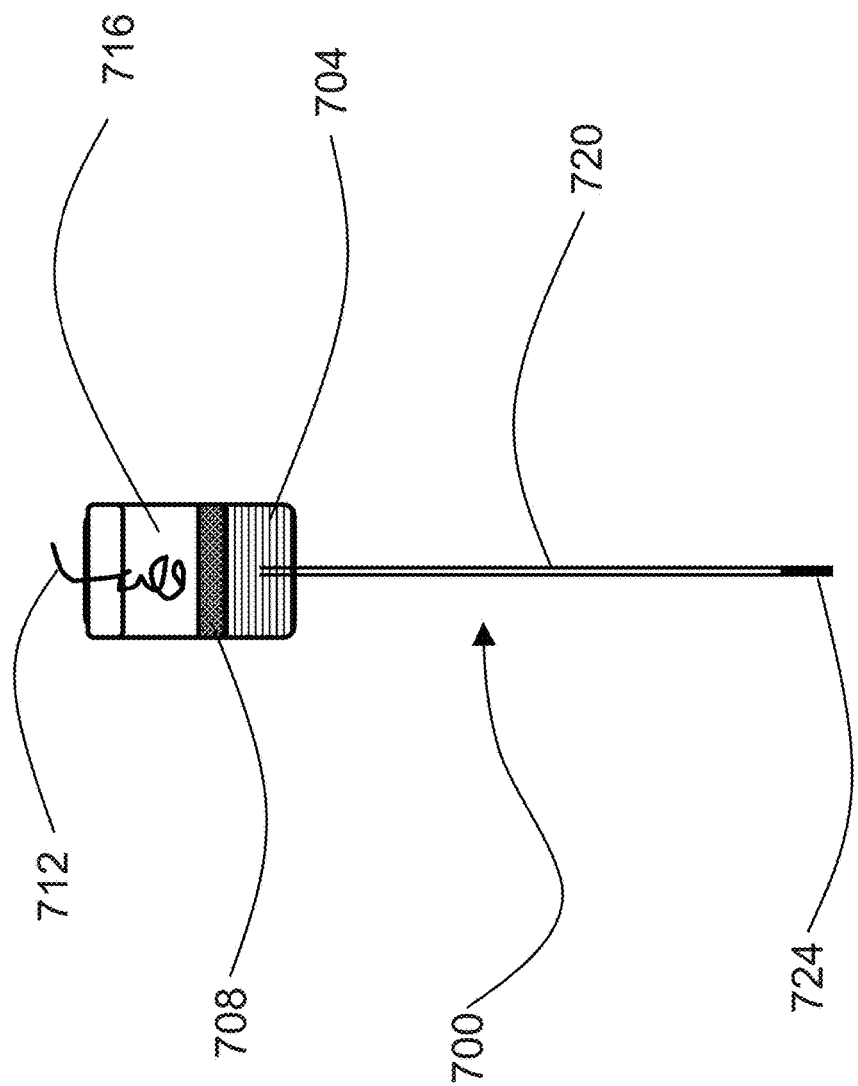
FIG. 7 displays a schematic of a hollow fiber probe embodiment of the present invention.

In other embodiments, the present invention may be implemented using hollow fiber probes, as shown in FIG. 7. Such hollow fiber probes may have two parts. One is a delivery tube or catheter that serves as a conduit for the solution being delivered. The second part may be located at the distal end of the probe, i.e. the end which is placed into the target tissue. The second part of the hollow fiber probe may be a porous hollow fiber such as those used in microdialysis. See Ungerstedt, U. "Microdialysis—principles and applications for studies in animals and man." *J. Intern. Med.* (1991) 230:365-373, which is hereby incorporated by reference. Other embodiments of the hollow fiber probe implementation of the present invention are similar to those used in pressure-induced convection-enhanced delivery. See Oh, S. et al. "Improved distribution of small molecules and viral vectors in the murine brain using a hollow fiber catheter." *J. Neurosurg.* (2007 September) 107 (3):568-77, which is hereby incorporated by reference.

When practicing the present invention using a hollow fiber probe 700, the proximal end (i.e., the opposite end to that which will be inserted into the tissue) probe may be placed in a vial with the solution to be delivered in a compartment 704, as shown in FIG. 7. A frit 708 or other separator may split the vial into two compartments of the probe to avoid electrochemical reactions from altering the solution to be delivered. The electrode 712 may be located in one compartment 716 which may contain buffer and the solution to be delivered is held in the compartment 704. Compartments 716 and 704 may be completely separate or connected by a flexible tube. Compartment 704 containing the solution to be delivered is connected to a catheter 720 such as a fused silica catheter or other catheter type as described above. A flexible tube (not shown) may be used to connect compartment 704 with catheter 720. In FIG. 7, catheter 720 is connected to a hollow fiber 724. A thin, solid support rod may be used in the lumens of catheter 720 and the hollow fiber 724 to support the hollow fiber 724 which may not naturally have the structural integrity to withstand implantation into tissue. Many other ways to arrange elements 712, 716, 708, 704, and optional flexible tubing are possible as is well known to electrochemists, such as placing the electrode in a separate compartment completely or by bending the probe.

In the experiments described below, the distal end of the hollow fiber catheter was a hollow fiber having a 280 µm inside and 360 µm outside diameter, and a length of 3-4 mm (724). A 10- or 15-cm long fused silica catheter (450 µm inside and 670 µm outside diameters, 720) directs fluid to the hollow fiber probe. The 100 µm inside diameter infusion catheter 720 was filled with the fluorophore solution of interest, as detailed below, in a glucose-free HEPES-buffered salt solution (GF-HBSS), containing in mM: 143.4 NaCl, 5 HEPES, 5.4 KCl, 1.2 $MgSO_4$, 1.2 $NaH_2PO_4$, and 2.0 $CaCl_2$. The probe was placed in a vial containing the same solution (704) through a septum. The 100 µm counter catheter was filled with GF-HBSS alone. The proximal end of the counter catheter was also immersed into a vial containing the same buffer solution.

Experiments using a hollow fiber probe were carried out in adult Sprague-Dawley rats. Rats were anesthetized with isoflurane. A craniotomy was created to allow access to the striatum (from bregma: 3.0 mm lateral, 0.7 mm posterior, and 5.0 mm below the dura). The striatum was chosen because of its comparably large size in the rat brain. A hollow fiber probe (Twin Star Medical) with an approximately 3 mm long hollow fiber portion was placed into the striatum of one cerebral hemisphere. The hollow fiber probe was used to deliver fluorescent molecules, thus allowing a simple determination of the distribution of the delivered compound. In particular, two fluorescent molecules were used: one is a small, cationic complex—the chloride salt of tris(2,2'-bipyridyl)ruthenium(II) ($Ru(bpy)_3^{2+}$); the other is a nearly neutral 70 kDa dextran that is fluorescently labeled with Texas Red (Table 1). The solution in the experiments here contained either a 45 mM solution of $Ru(bpy)_3^{2+}$ in GF-HBSS or a solution of 0.1 mM of the 70 kDa dextran. The solution was delivered via the methods of the present invention by applying a current of 25.0 µA for 30 or 45 minutes.

After the electrokinetic infusion period, the rats underwent rapid transcardial perfusion with 250 mL of 8% cold paraformaldehyde in phosphate buffer solution. The brain was immediately isolated, sectioned into 4 mm coronal slices, and then further sectioned on a vibratome into 200 µm thick coronal slices. Vibratome sectioning was quantitative, with no discarded tissue between slices with a visible fluorophore spot. The time required for the transcardial perfusion and vibratome sectioning was less than 30 minutes, while the transcardial perfusion itself was completed in less than 5 minutes. The 200 µm thick coronal slices were mounted onto glass slides and imaged with an inverted fluorescence microscope.

The volumes of distribution from the infusions were determined by measuring the fluorescence intensities in each coronal slice. The fluorescent area in each image was determined by counting pixels above a threshold value dictated by the noise level in the background (nonfluorescent portion of the image). The fluorescent area within each slice was multiplied by the thickness of the slice to arrive at a volume per tissue slice. The volumes of each slice were summed to arrive at a final volume of distribution for each rat and fluorophore.

For two experiments with $Ru(bpy)_3^{2+}$, the volume measured was 9.0 µL (25 µA and 45 minutes). For three experiments with 70 kDa TR-labeled dextran, an 4.7 µL average volume (5.3 and 4.1 µL) for 30 minute infusions and 8 µL for a single infusion for 45 minutes was observed.

Figure 8:
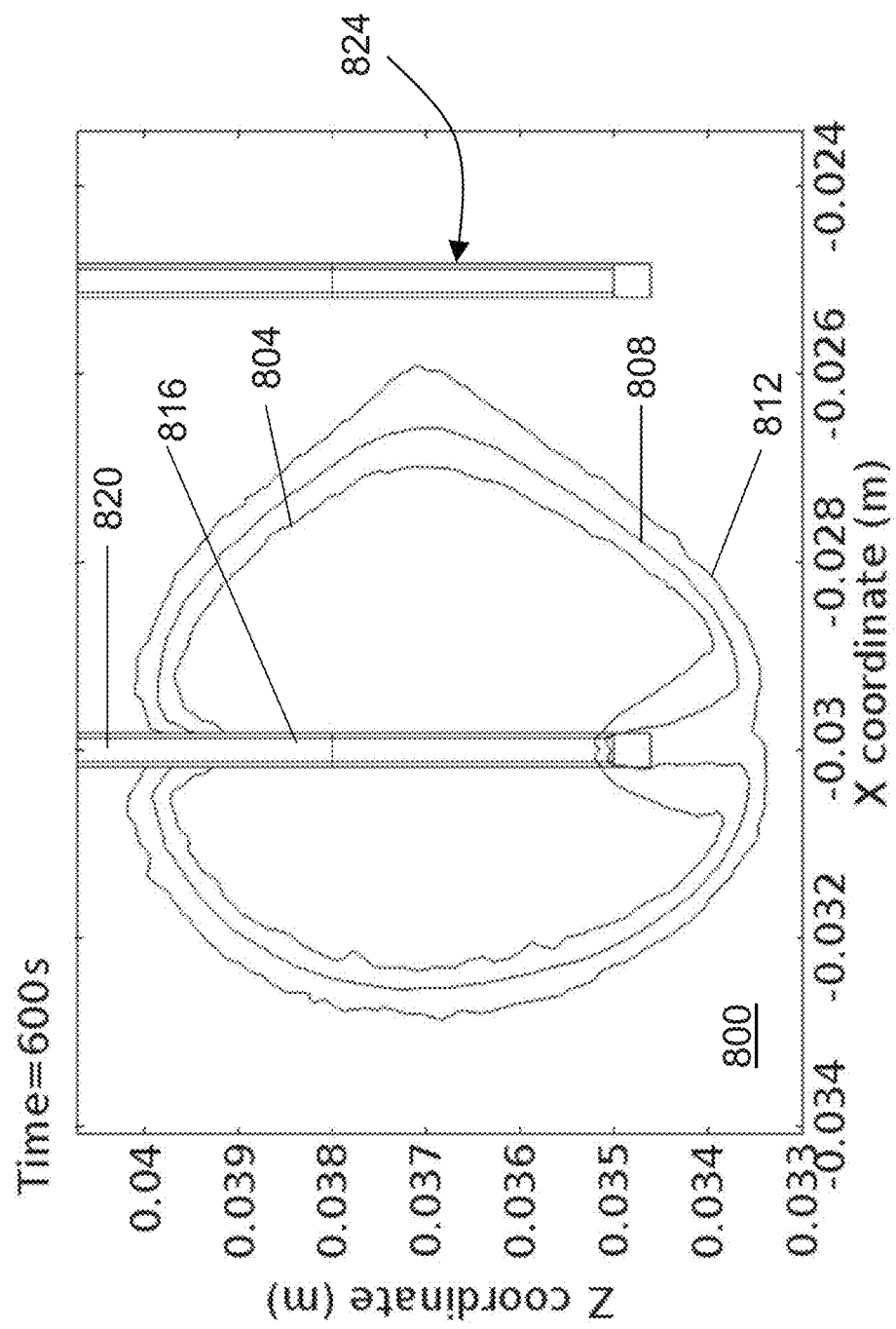
FIG. 8 presents a plot of the simulation of electroosmotic convection-enhanced delivery.

Computational experimental results are shown in FIG. 8. The concentration of the 70,000 MW dextran solute in the brain 800 is plotted as a set of contours (804, 808, and 812 are 90%, 50%, and 10% of the concentration in the catheter, respectively). The hollow fiber portion 816 of the infusion probe is attached to a fused silica portion 820 of the catheter. The counter-electrode 824 (shown on the right-hand side) may be an open electrode, hollow tube catheter (as shown), or any other sink for the current.

According to approximate theory, the flow rate of fluid in the extracellular space is directly proportional to the current applied and to the sum of the electroosmotic mobility (of the extracellular fluid) and the electrophoretic mobility of the particular solute (e.g., drug). The total volume infused is determined by the time of the infusion and the flow rate (volume/time). The infusion of larger volumes using larger currents (which would be impractical in the rat) was simulated. The fully three-dimensional simulations were carried out with COMSOL. Specifically, the DC electrical module calculated the electric field for a particular current. Then the Brinkmann equation for fluid flow in a porous medium was used to determine the fluid velocities in the tissue. Finally, the "dilute species" module was used to calculate the movement of the solute by diffusion and convection. Properties of the brain that affect drug transport were estimated by Guy, et al. (2008); Guy, et al. (2009); Kim, et al. "A voxelized model of direct infusion into the corpus callosum and hippocampus of the rat brain: model development and parameter analysis." *Med. Biol. Eng. Comput.*, (2010) 48:203-14; or Stoverud, K.; Darcis, M.; Helmig, R.; Hassanizadeh, S. M. "Modeling Concentration Distribution and Deformation During Convection-Enhanced Drug Delivery into Brain Tissue." *Transport in Porous Media*, (2012) 92:119-43 (which are hereby incorporated by reference). These properties, used for determining the electroosmotic velocity in the tissue are listed as Table 2 ("brain" specifically refers to gray matter)::

| | |
|---|---|
| Electrical conductivity of brain | 0.11 S/m |
| Dynamic viscosity of ecf | 0.001 Pa · s |
| Permeability of brain | $1.0 \times 10^{-15}$ $m^2$ |
| Porosity of brain | 0.2 |
| Tortuosity of brain | 1.61 |
| Tissue ζ-potential | −0.0213 V |
| Electrical conductivity of brain | 0.11 S/m |
| Dynamic viscosity of ecf | 0.001 Pa · s |

In addition, within the catheter, the wall zeta-potential is −0.050 V and the conductivity is 1.4 S/m. An infusion into a brain significantly larger than a rat's was simulated. The catheter had a 3 mm length of a porous wall as in Oh, S. et al. (2007). The current was 2 mA applied for 10 minutes. FIG. 8 demonstrates the result (it is a slice of the full three-dimensional simulation). The approximate relationship shown above can be used to estimate that the flow rate should be about 1.5 µL/minute. With a porosity of 0.2 and a time of 10 minutes, the volume of the observed infusion is predicted to be about 75 µL. The more accurate computations described in the preceding paragraph find a flow rate of 2.07 µL/minute leading to a volume of infusion of 104 µL. As can be seen from the scale in FIG. 8, the infusion indeed occupies approximately 100 µL.

FIG. 8 demonstrates also the important characteristic of directionality. The flow tends to go towards the counter probe rather than away from it. The current decays approximately as 1/r (r=distance from the cylindrical hollow fiber) in this case, thus hollow fiber catheters are more capable than simple open tube catheters in directing flow in a particular direction.

The present invention encompasses methods of administering a solution that may or may not contain a drug or solute (e.g., biologically active small molecule, antibody, other solute) through electroosmotic transport to a human or animal subject in need thereof. Additionally, the present invention may be used to transport interstitial fluid without administering a drug to the subject. This process may be useful in relieving tissue edema or swelling. The process may be useful in moving fluid from one region of the brain to an adjacent region. For example, drug may be injected into a ventricle by ordinary means and then subsequently driven by electroosmosis into nearby tissue. The above-described experiments establish that such administration may be reproducibly achieved without damaging tissue. Additionally, the present invention may also be employed to administer drugs to human or animal subjects through electroosmotic transport from any drug-containing reservoir, such as a drug-containing catheter or a doped infusion pad. The use of a chronically implanted, doped infusion pad or catheter in electroosmotic transport may allow sustained administration of a biologically active substance over an extended period of time.

The present invention also encompasses apparatuses used to deliver biological active substances to a subject via electroosmotic transport. Such apparatuses may include a drug-containing reservoir such as a catheter or infusion pad, a counter-electrode, and a current generator. The current generator preferably has appropriate circuitry to allow administration of sufficient current to administer clinically effective amounts of the bioactive substance to the subject. One of skill in the art is familiar with a diversity of such current generators. The specific pattern and intensity of current administration will change for different applications of the present invention and compounds used. One of skill in the art will readily be able to identify the appropriate parameters through routine experimentation.

One of skill in the art will recognize that the present invention may be implemented employing a wide variety of components and for a diversity of bioactive agents. For example, the catheters that may be employed within the context of the present invention may be made from borosilicate, quartz, fused silica, plastic, mineral oxides (e.g., silica, titanium, zirconia), ceramics, and composite materials containing polymers and fillers. The catheters may also be fabricated from metals that are coated with a material to prevent significant current flow through the coated metal. The catheters may be stiff or flexible depending on the specific situation in which the present invention is employed.

The size of the catheters may also be varied, depending on the specific application of the present invention. For example, the catheters may be shaped in various ways, including circular or elliptical with a constant radius or having a conical tip (the portion in the tissue) which may have an opening as small as about 1 μm in diameter up to several millimeters. The catheters of the present invention may be round in cross section, substantially square, curved, arced, or in any other geometry and the particulars of the implementation require. Capillaries, tubes or other conduits may be grouped together to form multiple-barreled delivery systems. The infusate need not be directed out the open tip of the delivery tube. The wall of the tube may be porous or perforated in places to permit flow at several spots along the wall.

Additionally, the present invention may be employed to deliver a wide diversity of bioactive compounds to subjects. Compounds having a strongly positive charge are particularly preferred within the context of the present invention, though compounds with any potential other than those small, negative compounds with electroosmotic mobilities that are negative and greater (in absolute value) than the tissue electroosmotic mobility may be used. Furthermore, one of skill in the art will recognize that while the present invention has been described with regards particularly to administration of bioactive agents into the brain, the present invention may also be employed to administer such compounds to any organ or location within the body.

Nothing in the above description is meant to limit the present invention to any specific materials, geometry, or orientation of elements. Many modifications are contemplated within the scope of the present invention and will be apparent to those skilled in the art. The embodiments described herein were presented by way of example only and should not be used to limit the scope of the invention.

The invention claimed is:

1. A method of administering a fluid to a tissue, comprising:
   inserting a blunt end of a distal portion of at least one fluid passage defined by a hollow fiber into a target tissue at a first position in a subject;
   fluidically coupling a proximal portion of the at least one fluid passage defined by the hollow fiber to a fluid reservoir with a catheter, wherein a support rod is situated in lumens of the hollow fiber and the catheter;
   placing a counter-electrode at a second subject position, wherein the fluid reservoir and the counter-electrode are operably connected to a current source;
   applying a current to the fluid reservoir; and
   allowing the fluid to be transported into the tissue in response to the applied current.

2. The method of claim 1, wherein said tissue is a neural tissue.

3. The method of claim 1, further comprising implanting the catheter in said target tissue.

4. The method of claim 1, wherein a path between said first position and said second position defines a trajectory along with an electrokinetic transport occurs.

5. The method of claim 1, wherein said fluid is a drug-containing fluid.

6. The method of claim 5, wherein said drug is a small molecule or a peptide.

7. The method of claim 6, wherein said small molecule is a chemotherapeutic compound, a local anesthetic, a neurotransmitter, or a steroid.

8. The method of claim 6, wherein said peptide is a neurotransmitter, an antibody, or a signaling peptide.

9. The method of claim 5, wherein said drug is a positively charged molecule.

10. The method of claim 5, wherein said drug is a neutral molecule.

11. The method of claim 5, wherein said drug is a negatively charged molecule.

12. The method of claim 5, wherein said drug-containing fluid includes a drug in a formulation of nanoparticles or liposomes.

13. The method of claim 1, wherein the fluid reservoir situated remote from said subject and the current is directed to the fluid in the fluid reservoir with an electrode situated at the fluid reservoir.

14. The method of claim 1, wherein the current is directed toward the subject from said fluid reservoir situated external to said subject through the at least one fluid passage.

15. The method of claim 1, wherein the current is directed between the fluid reservoir and the tissue through the fluid passage defined in the hollow fiber.

16. The method of claim 1, further comprising providing the fluid reservoir in a first compartment of a vial, wherein the vial includes a second compartment and a separator situated between the first compartment and the second compartment, wherein an electrode is situated in the second compartment so that the current is applied to the first compartment of the fluid reservoir from the second compartment of the fluid reservoir through the separator with the electrode in the second compartment.

17. The method of claim 1, wherein the fluid passage is defined by a methacrylate-, acrylate-, or sulfonate-containing polymer.

18. The method of claim 1, wherein the fluid passage is defined by an anionic surface.

* * * * *